US012596100B2

(12) United States Patent　　(10) Patent No.: US 12,596,100 B2

Qi et al.　　(45) Date of Patent: Apr. 7, 2026

(54) DEVICE FOR DETECTING DEFECT IN STEEL CORD

(71) Applicant: WEIHAI HUALING OPTO-ELECTRONICS CO., LTD., Weihai (CN)

(72) Inventors: Wuchang Qi, Weihai (CN); Kai Zhang, Weihai (CN); Xiaofeng Sun, Weihai (CN); Pengtong Wang, Weihai (CN); Mingfeng Sun, Weihai (CN); Rongxin Song, Weihai (CN)

(73) Assignee: WEIHAI HUALING OPTO-ELECTRONICS CO., LTD., Weihai (CN)

( * ) Notice: Subject to any disclaimer, the term of this patent is extended or adjusted under 35 U.S.C. 154(b) by 179 days.

(21) Appl. No.: 18/510,589

(22) Filed: Nov. 15, 2023

(65) Prior Publication Data

US 2024/0085375 A1　　Mar. 14, 2024

Related U.S. Application Data

(63) Continuation of application No. PCT/CN2022/091908, filed on May 10, 2022.

(30) Foreign Application Priority Data

Sep. 3, 2021　(CN) ......................... 202111034190.5

(51) Int. Cl.
　G01N 27/82　　(2006.01)
　G01N 33/2045　　(2019.01)
(52) U.S. Cl.
　CPC ......... G01N 27/82 (2013.01); G01N 33/2045 (2019.01)

(58) Field of Classification Search
　CPC ..... G01N 27/82; G01N 27/83; G01N 33/2045
　See application file for complete search history.

(56) References Cited

U.S. PATENT DOCUMENTS

| | | | |
|---|---|---|---|
| 3,670,239 A | 6/1972 | Shiraiwa et al. | |
| 5,034,690 A | 7/1991 | Taliaferro | |
| | (Continued) | | |

FOREIGN PATENT DOCUMENTS

| | | |
|---|---|---|
| CN | 101266226 A | 9/2008 |
| CN | 101995432 A | 3/2011 |
| | (Continued) | |

OTHER PUBLICATIONS

The World Intellectual Property Organization (WIPO) International Search Report for PCT/CN2022/091908 Jul. 19, 2022 6 pages (with translation).

(Continued)

*Primary Examiner* — Dominic E Hawkins

(74) *Attorney, Agent, or Firm* — Scully, Scott, Murphy & Presser, P.C.

(57)　　ABSTRACT

The present application provides a device for detecting a defect in a steel cord ply. The device is configured to obtain an enhanced magnetic field signal of the steel cord ply and detect a defect of the steel cord ply based on the enhanced magnetic field signal. The device includes a magnetic field unit including a permanent magnet configured to generate a background magnetic field; a signal obtaining unit configured to generate an enhanced magnetic field signal of a steel cord ply based on a plurality of first magnetic field signals and a plurality of second magnetic field signals; and a defect detecting unit configured to detect a defect of the steel cord ply based on the enhanced magnetic field signal, wherein the defect detecting unit includes an AD converting module, a (Continued)

signal processing module, a defect detecting module, a display module, and a control module.

8 Claims, 7 Drawing Sheets

(56)                References Cited

U.S. PATENT DOCUMENTS

| | | | | |
|---|---|---|---|---|
| 6,005,388 | A * | 12/1999 | Kaefer-Hoffmann ........................ | |
| | | | | G01N 27/82 |
| | | | | 73/146 |
| 9,994,429 | B1 * | 6/2018 | Taniguchi ............. | B66B 25/006 |
| 11,190,864 | B1 * | 11/2021 | Vandyke ................ | H04R 1/028 |
| 2015/0130454 | A1 | 5/2015 | Itoi et al. | |
| 2015/0176962 | A1 | 6/2015 | Kerdraon et al. | |
| 2017/0370806 | A1 | 12/2017 | Schober et al. | |
| 2021/0223206 | A1 * | 7/2021 | Iijima .................. | G01N 27/904 |
| 2021/0380372 | A1 * | 12/2021 | Iijima .................... | G01N 27/87 |

FOREIGN PATENT DOCUMENTS

| | | | |
|---|---|---|---|
| CN | 105092698 | A | 11/2015 |
| CN | 107607892 | A | 1/2018 |
| CN | 108776171 | A | 11/2018 |
| CN | 109141482 | A | 1/2019 |
| CN | 109632941 | A | 4/2019 |
| CN | 110187005 | A | 8/2019 |
| CN | 112834605 | A | 5/2021 |
| CN | 113820386 | A | 12/2021 |
| CN | 215894477 | U | 2/2022 |
| JP | H06316394 | A | 11/1994 |
| JP | H06317563 | A | 11/1994 |
| JP | H1010060 | A | 1/1998 |
| JP | 2006317218 | A | 11/2006 |
| JP | 2016105061 | A | 6/2016 |
| JP | 2017198601 | A | 11/2017 |
| JP | 2018146323 | A | 9/2018 |
| WO | 2014016978 | A1 | 7/2016 |

OTHER PUBLICATIONS

The first Office Action of the priority CN patent application No. 202111034190.5, mail date Jun. 12, 2024.

The Notification of grant of patent right for invention of the priority CN patent application No. 202111034190.5, mail date Oct. 31, 2024.

The first Office Action of the corresponding KR patent application No. 10-2023-7034465, mail date Jan. 4, 2025.

The extended European search report of the corresponding EP patent application No. 22862704.8, mail date Jul. 24, 2024.

The first Office Action of the corresponding JP patent application No. 2023-579774, mail date Jan. 7, 2025.

* cited by examiner

DEVICE FOR DETECTING DEFECT IN STEEL CORD PLY

MAGNETIC FIELD UNIT

DEFECT DETECTING UNIT

CONTROL MODULE

DEFECT DETECTING MODULE

SIGNAL OBTAINING UNIT

MAGNETIC SENSOR MODULE

AD CONVERTING MODULE

CALCULATING MODULE

DIFFERENTIAL MODULE

SIGNAL PROCESSING MODULE

DEFECT PROCESSING MODULE

SIGNAL OUTPUT MODULE

DISPLAY MODULE

ALARM MODULE

TYPE OF DEFECT: CORD DOUBLING          TYPE OF DEFECT: CORD MISSING

DEVICE FOR DETECTING DEFECT IN STEEL CORD

RELATED APPLICATION

This application is a continuation application of PCT Application Serial No. PCT/CN2022/091908, filed on May 10, 2022, which claims priority to Chinese Patent Application No. 202111034190.5, filed on Sep. 3, 2021, the content all of which is herein incorporated by reference in their entirety.

TECHNICAL FIELD

The present application generally relates to the field of industrial nondestructive testing and, more particularly, relates to a device capable of detecting a defect in a steel cord ply based on an enhanced magnetic field signal of the steel cord ply.

BACKGROUND

Steel cord plies are important parts of truck tires. A steel cord ply includes an outer rubber layer and steel cords wrapped in the rubber layer and spaced at equal intervals. As a belt layer of a truck tire, the steel cord ply provides important support for enhancing the structural strength and bearing capacity of the truck tire. During the manufacturing process of the steel cord ply, due to the influence of the production equipment and the process flow, steel wires in the steel cord ply may have situations of uneven distribution, such as bending, dislocation, disconnection, crossing, etc. If the distribution condition of the steel wires in the steel cord ply cannot be detected in real-time, the quality of the steel cord ply will be adversely affected, and the performance and safety of the truck tire may be directly affected.

Existing nondestructive testing techniques for steel cord plies include a non-destructive testing method based on X-rays, a non-destructive testing method based on electromagnetic induction principles, etc. In particular, in the nondestructive testing method based on electromagnetic induction, the change of a magnetic field of the steel cord ply, which is caused by the movement of the steel cord ply in the magnetic field, is used to detect the steel cords inside the steel cord ply, and this method is economical, safe and convenient.

However, the existing devices for detecting a defect of a steel cord ply based on a magnetic field generally have the following problems.

First, the magnetic field detection unit used includes a general-purpose magnetic head and a coil, and its volume is often much larger than the arrangement cycle of steel wires in the steel cord ply. The detected magnetic field changes are the result of the superposition of magnetic field changes caused by multiple steel wires, resulting in a low accuracy of the detection result, and other problems such as missed detection and false detection. Additional processing steps for missed detection and false detection need to be set, which is not conducive to real-time defect detection of the steel cord ply.

Second, it has a higher requirement for the placement position of the magnetic field detection unit. Especially, the strength of the background magnetic field and the distribution of magnetic force lines have a greater impact on the detection results.

In order to solve the problems existing in the above defect detection technology of steel cord plies, the present application is proposed.

SUMMARY

The purpose of the present application is to provide a device for detecting a defect in a steel cord ply, which can obtain the enhanced magnetic field signal of the steel cord ply and detect the defect of the steel cord ply based on the enhanced magnetic field signal.

Exemplary embodiments of this application can be realized through the following technical solutions.

A device for detecting a defect of a steel cord ply, which is configured to obtain an enhanced magnetic field signal of the steel cord ply and detect a defect of the steel cord ply based on the enhanced magnetic field signal, includes: a magnetic field unit including a permanent magnet configured to generate a background magnetic field; a signal obtaining unit configured to generates an enhanced magnetic field signal of a steel cord ply based on a plurality of first magnetic field signals and a plurality of second magnetic field signals; and a defect detecting unit configured to detect a defect of the steel cord ply based on the enhanced magnetic field signal. The signal obtaining unit includes: a magnetic sensor module configured to generate the plurality of first magnetic field signals and the plurality of second magnetic field signals, a differential module connected to the magnetic sensor module and configured to generate a plurality of differential magnetic field signals based on the plurality of first magnetic field signals and the plurality of second magnetic field signals, and a signal output module connected to the differential module and including input terminals configured to receive the plurality of differential magnetic field signals and at least one output terminal, wherein the signal output module is configured to generate and output the enhanced magnetic field signal based on the plurality of differential magnetic field signals. The defect detecting unit includes an AD converting module, a signal processing module, a defect detecting module, a display module, and a control module.

Further, the magnetic sensor module includes: a plurality of first magneto-sensitive elements configured to sense a change of a magnetic field caused by a movement of the steel cord ply in the background magnetic field and generate the plurality of first magnetic field signals; and a plurality of second magneto-sensitive elements configured to sense a change of a magnetic field caused by the movement of the steel cord ply in the background magnetic field and generate the plurality of second magnetic field signals. The plurality of first magnetic field signals and the plurality of second magnetic field signals are electrical signals.

Further, the plurality of first magneto-sensitive elements corresponds to the plurality of second magneto-sensitive elements in a one-to-one way, and a spacing distance between each first magneto-sensitive element and a corresponding second magneto-sensitive element along a moving direction of the steel cord ply is half of a spacing distance between adjacent steel cords of the steel cord ply along the moving direction of the steel cord ply.

Further, the plurality of first magneto-sensitive elements is distributed at intervals along a direction perpendicular to the moving direction of the steel cord ply; and the plurality of second magneto-sensitive elements are distributed at intervals along a direction perpendicular to the moving direction of the steel cord ply.

Further, the differential module includes a plurality of differential circuits, and the plurality of differential circuits are connected to the plurality of first magneto-sensitive elements and the plurality of second magneto-sensitive elements in one-to-one correspondence; and one end of the differential circuit is connected to the first magneto-sensitive element, and the other end of the differential circuit is connected to the second magneto-sensitive element, and output terminals of the plurality of differential circuits are connected to the input terminals of the signal output module.

Further, the magnetic field unit includes a magneto-conductive plate located on a surface of a side of the permanent magnet that faces toward the steel cord ply, and the magneto-conductive plate is made of a magneto-conductive material.

Further, the AD converting module is connected to the signal output module and configured to convert the enhanced magnetic field signal into a digital magnetic field signal; the signal processing module is configured to process the digital magnetic field signal to generate a magnetic field signal to be detected; the defect detecting module is configured to analyze the magnetic field signal to be detected and generates a defect detection result of the steel cord ply; the display module is configured to display the magnetic field signal to be detected and the defect detection result of the steel cord ply; and the control module is configured to control the AD converting module, the signal processing module, the defect detecting module, and the display module.

Further, the defect detecting unit includes: a calculating module configured to determine defect marking information according to the defect detection result of the steel cord ply and a moving speed of the steel cord ply, wherein the defect marking information includes mark position information and a mark trigger time; a defect processing module configured to mark a defect according to the defect marking information; and alarm module configured to raise an alarm when an abnormal situation occurs.

Further, the device includes a frame, where the magnetic field unit and the signal obtaining unit are fixedly installed in the frame.

Further, a surface of a side of the frame that faces toward the steel cord ply is a cover.

The defect detection system provided by the present application has at least the following beneficial effects.

First, the interval between the plurality of first magneto-sensitive elements and the plurality of second magneto-sensitive elements arranged at intervals along the moving direction of the steel cord ply is set to be half of the interval between adjacent steel wire cords in the steel cord ply along the moving direction of the steel cord ply so that a magnetic field signal delayed by half a cycle can be generated, and an enhanced magnetic field signal of the steel cord ply obtained by differential processing of multiple differential circuits can offset the background magnetic field signal and at the same time enhance the strength of the magnetic field signal of the regularly arranged steel cords. Compared with the situation where the signal is obtained by a single magneto-sensitive element and superimposed with the background magnetic field signal, the signal-to-noise ratio can be effectively improved.

Second, by offsetting the background magnetic field signal, the influence of the placement position of the magnetic field unit on the obtained enhanced magnetic field signal is greatly weakened, thereby addressing the problem of low accuracy of the magnetic field signal caused by the uneven distribution of magnetic force lines of the background magnetic field.

Figures 1, 2:
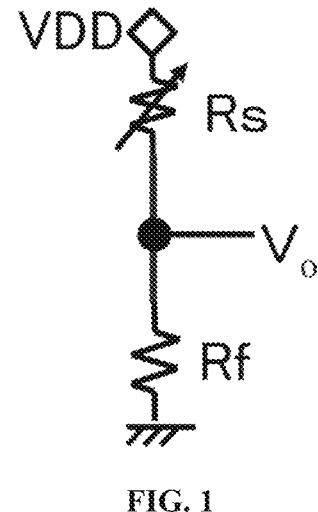
FIG. 1 is an electrical schematic diagram of a magneto-sensitive element obtaining an output magnetic field signal.
FIG. 2 is a system block diagram of a defect detecting device for steel cord ply according to exemplary embodiments of the present application.

Label in the figure: magnetic field unit 11, permanent magnet 111, magneto-conductive plate 112, signal obtaining unit 22, magnetic sensor module 221, first magneto-sensitive element 2211, second magneto-sensitive element 2212, differential module 222, differential circuit 2220, signal output module 223, steel cord ply 41, frame 51, cover 511, substrate 61, signal connection line 70.

DETAILED DESCRIPTION

Examples of the present application will be further described based on preferred implementations with reference to the drawings.

In addition, for the convenience of understanding, various components on the drawings may be enlarged (thickened) or reduced (thinned), but this approach is not intended to limit the scope of protection of the present application.

Words in the singular form may also include the plural form and vice versa.

In the description of the embodiments of the present application, it should be noted that the orientational or positional relationships indicated by the terms "upper", "lower", "inner" and "outer" and the like are based on the orientational or positional relationships shown in the drawings, or the orientational or positional relationship that the product of this embodiment is usually placed in use, and this is only for the convenience of describing the present application and simplifying the description, rather than indicating or implying that the mentioned device or element must have a specific orientation, or being configured or operated in a specific orientation, and therefore should not be construed as limiting the present application. In addition, in the description of the present application, in order to distinguish different units, words such as first and second are used in this specification, but these are not limited by the order of manufacture, nor can they be interpreted as indicating or implying relative importance. The terms may vary in the detailed description and the claims of the present application.

The terms in this specification are used to describe the embodiments of the present application but are not intended to limit the present application. It should also be noted that, unless otherwise clearly stipulated and limited, the terms "set", "connected" and "attached" should be interpreted in a broad sense, for example, it can be a fixed connection, a detachable connection, or an integral connection; it can be a mechanical connection, a direct connection, or an indirect connection through an intermediary, or an internal connection between two components. Those skilled in the art can especially understand the specific meanings of the above-mentioned terms in the present application.

In order to better illustrate the technical solution of embodiments of the present application, we first introduce the working principle of magnetic field signal acquisition by a magnetic sensor with reference to FIG. 1.

FIG. 1 is an electrical schematic diagram of a magneto-sensitive element obtaining a magnetic field signal. As shown in FIG. 1, the magneto-sensitive element is a component that can sense a magnetic field and convert a magnetic field signal into an electrical signal for output. The magneto-sensitive element includes a magneto-sensitive resistor and a reference resistance that are connected in series, where the resistance Rs of the magneto-sensitive resistor varies with the sensed change of the magnetic field, and the resistance Rf of the reference resistance is a constant value.

When it is necessary to obtain a magnetic field signal, the magneto-sensitive element is placed in a background magnetic field, and as shown in FIG. 1, a voltage VDD is applied to an end of the magneto-sensitive element with the other end grounded. At the same time, an output voltage Vo is introduced from between the magnetic sensitive resistor and the reference resistor. At this time, the resistance Rs of the magneto-sensitive resistor is a resistance corresponding to the background magnetic field. According to the principle of voltage division, Vo=VDD*Rf/(Rf+Rs), and the output voltage signal Vo is a signal reflecting the background magnetic field.

When an object containing magnetic material approaches and enters the background magnetic field, the movement of the magnetic material will cause a change in the background magnetic field, thereby causing a change in Rs, and further causing a change in the output voltage signal Vo. At this time, the output voltage signal Vo is a magnetic field signal that reflects changes in the location of each magneto-sensitive element.

In actual manufacturing and use, in order to obtain a wide range of magnetic field signals, a plurality of magneto-sensitive elements is generally arranged at intervals along a preset direction, and the magnetic field signals output by multiple magneto-sensitive elements are processed in parallel to serial and output in the form of serial magnetic field signals.

The detailed implementation of an embodiment of the present application will be described in detail below with reference to FIG. 2 to FIG. 13.

Figure 3:
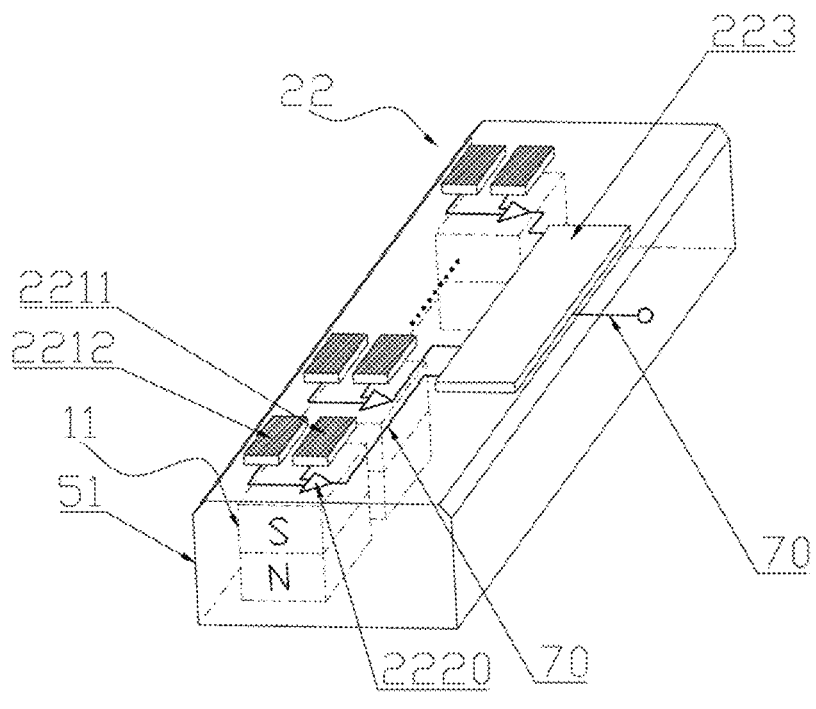
FIG. 3 is a perspective view of a detailed implementation according to exemplary embodiments of the present application.
Figure 4:
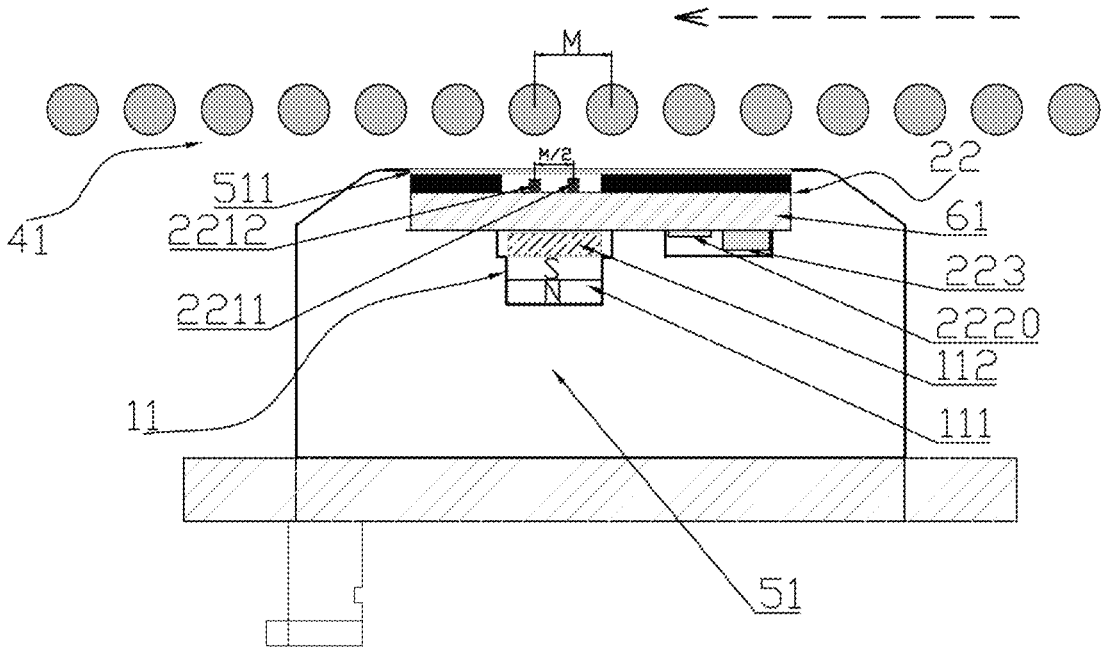
FIG. 4 is an assembled side view of a detailed implementation according to exemplary embodiments of the present application.

FIG. 2 is a system block diagram of a defect detecting device for steel cord ply according to exemplary embodiments of the present application, FIG. 3 is a perspective view of an embodiment of the present application (where a defect detecting unit is not shown in this figure), and FIG. 4 is an assembled side view of a detailed implementation according to exemplary embodiments of the present application (where a defect detecting unit is not shown in this figure).

As shown in FIGS. 2 to 4, an embodiment of the present application provides a defect detecting device for steel cord ply, which is used to obtain an enhanced magnetic field signal of the steel cord ply and detect a defect of the steel cord ply based on the enhanced magnetic field signal. The defect detecting device includes: a magnetic field unit 11 including a permanent magnet 111 for generating a background magnetic field; a signal obtaining unit 22 for generating an enhanced magnetic field signal for steel cord ply based on multiple first magnetic field signals and multiple second magnetic field signals; a defect detecting unit for detecting a defect of the steel cord ply based on the enhanced magnetic field signal, which includes an AD converting module, a signal processing module, a defect detecting module, a display module, and a control module.

In a detailed implementation of an embodiment of the present application, the magnetic field unit 11 and the signal obtaining unit 22 are fixedly installed in the frame 51.

For example, in a detailed implementation of an embodiment of the present application, a side of the frame 51 that faces toward a steel cord ply 41 (for clearly illustrating embodiments of the present application, the steel cord ply is represented by steel cords regularly distributed in the steel cord ply) may be provided with limiting slots for accommodation and fixation of the magnetic field unit 11 and the signal obtaining unit 22, wherein the signal obtaining unit 22 may be packaged on a circuit substrate 61, and the circuit substrate 61 is placed on the surface of a side of the magnetic field unit 11 that faces toward the steel cord ply 41. The magnetic field unit 11 may include a permanent magnet 111 whose long side is perpendicular to the moving direction of the steel cord ply 41 or may include a plurality of permanent magnets distributed at intervals with the direction of the interval distribution perpendicular to the moving direction of the steel cord ply 41.

Further, as shown in FIG. 4, the magnetic field unit 11 may include a magneto-conductive plate 112. The magneto-conductive plate 112 is located on the surface of a side of the permanent magnet 111 that faces toward the steel cord ply 41. The magneto-conductive plate 112 may be made of a magneto-conductive material.

For example, in exemplary embodiments of the present application, the magneto-conductive plate 112 may be made of materials such as iron plate, ferrite plate, permalloy plate, and/or silicon steel plate. The magneto-conductive plate 112 is located on the surface of a side of the permanent magnet 111 that faces toward the steel cord ply 41 for guiding magnetic field lines generated by the permanent magnet 111 to make the distribution of the intensity and the direction of the magnetic field lines more uniform.

For example, as shown in FIG. 4, the width of the cross-section of the permanent magnet 111 along the moving direction of the steel cord ply 41 is smaller than the spacing distance between adjacent steel cords of the steel cord ply 41 along the moving direction of the steel cord ply 41.

Through the above configuration, the magnetic field lines of the background magnetic field are concentratedly distributed within an interval period of the steel cords, which can eliminate the magnetic field disturbance caused by the steel cords outside the background magnetic field, thereby effectively reducing the influence of the disturbing magnetic field.

Figure 5:
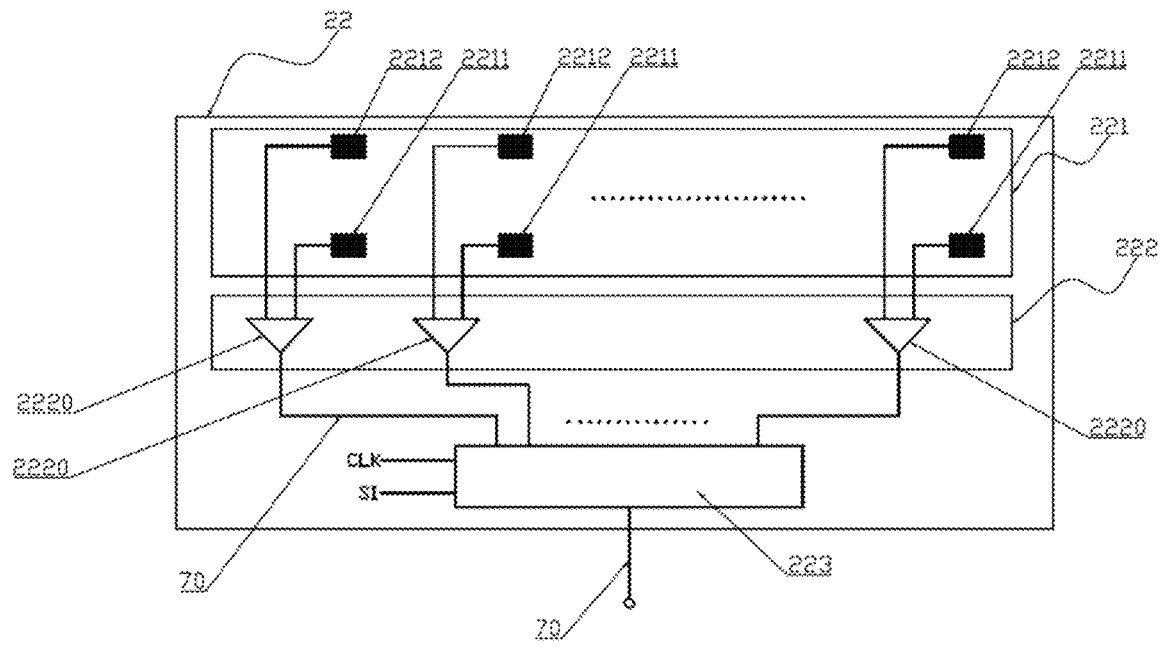
FIG. 5 is an electrical connection diagram of a signal obtaining unit according to exemplary embodiments of the present application.
Figure 6:
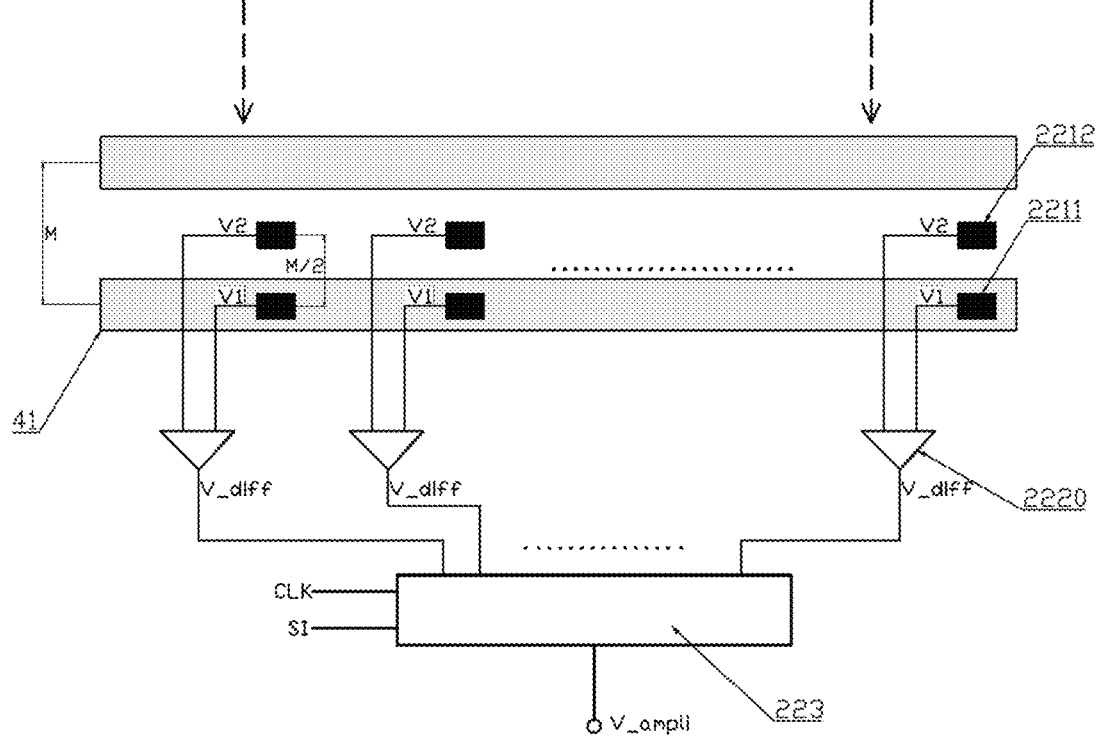
FIG. 6 is an electrical schematic diagram of a signal obtaining unit according to exemplary embodiments of the present application.

The structure and technical solution of the signal obtaining unit 22 of an embodiment of the present application will be described in detail below with reference to FIG. 3 to FIG. 6. FIG. 5 is an electrical connection diagram of the signal obtaining unit 22 of an embodiment of the present application, and FIG. 6 is a diagram of the working principle of the signal obtaining unit 22 according to exemplary embodiments of the present application.

As shown in FIGS. 3 to 6, the signal obtaining unit 22 includes: a magnetic sensor module 221 configured to generate a plurality of first magnetic field signals and a plurality of second magnetic field signals; a differential module 222 connected with the magnetic sensor module 221 and configured to generate a plurality of differential magnetic field signals based on the plurality of first magnetic field signals and the plurality of second magnetic field signals; and a signal output module 223 connected to the differential module 222 and including a plurality of input terminals for receiving the plurality of differential magnetic field signals and at least one output terminal for generating and outputting an enhanced magnetic field signal based on the plurality of differential magnetic field signals.

Further, the magnetic sensor module 221 includes: a plurality of first magneto-sensitive element 2211 configured to sense the change of the magnetic field caused by the movement of the steel cord ply 41 in the background magnetic field and generate the plurality of first magnetic field signals; and a plurality of second magneto-sensitive element 2212 configured to sense the change of the magnetic field caused by the movement of the steel cord ply 41 in the background magnetic field and generate the plurality of second magnetic field signals, where the plurality of first magnetic field signals and the plurality of second magnetic field signals are electrical signals.

Further, there is a one-to-one correspondence between the plurality of first magneto-sensitive element 2211 and the plurality of second magneto-sensitive element 2212, and the spacing distance between each first magneto-sensitive element 2211 and a corresponding second magneto-sensitive element 2212 along the moving direction of the steel cord ply 41 is half of the spacing distance between adjacent steel cords of the steel cord ply 41 along the moving direction of the steel cord ply 41.

Further, the plurality of first magneto-sensitive elements 2211 are distributed at intervals along a direction perpendicular to the moving direction of the steel cord ply 41, and the plurality of second magneto-sensitive elements 2212 are distributed at intervals along a direction perpendicular to the moving direction of the steel cord ply 41.

Further, the differential module 222 includes a plurality of differential circuits 2220, and the plurality of differential circuits 2220 is connected to the plurality of first magneto-sensitive elements 2211 and the plurality of second magneto-sensitive elements 2212 in a one-to-one correspondence.

Further, one end of the differential circuit 2220 is connected to the first magneto-sensitive element 2211, the other end of the differential circuit 2220 is connected to the second magneto-sensitive element 2212, and output terminals of the plurality of differential circuits 2220 are connected to a plurality of input terminals of the signal output module 223.

For example, in exemplary embodiments of the present application, the magnetic sensor module 221 includes a plurality of pairs of first magneto-sensitive element 2211 and second magneto-sensitive element 2212. The spacing distance between each pair of first magneto-sensitive element 2211 and second magneto-sensitive element 2212 along the moving direction of steel cord ply 41 is M/2, where M is the spacing distance between adjacent steel cords of the steel cord ply 41 along the moving direction of steel cord ply 41. Each first magneto-sensitive element 2211 outputs a magnetic field signal corresponding to its location in the form of an electrical signal V1 to an input terminal of a corresponding differential circuit 2220 through a signal connection line 70, and each second magneto-sensitive element 2212 outputs a magnetic field signal corresponding to its location in the form of an electrical signal V2 to another input terminal of the corresponding differential circuit 2220 through the signal connection line 70.

The plurality of differential circuits 2220 perform differential processing on a plurality of V1 and V2 respectively to obtain a plurality of differential magnetic field signals V_diff, and the output terminal of each differential circuit 2220 is connected to the input terminal of the signal output module 223 through the signal connection line 70 and is used to output the differential magnetic field signal V_diff to the signal output module 223.

The signal output module 223 includes a plurality of input terminals for receiving the above-mentioned plurality of output differential magnetic field signals. The signal output module 223 also includes at least an output terminal, a clock signal terminal for receiving a clock signal CLK and a start signal terminal for receiving a start signal SI. The signal output module 223, after receiving the start signal SI, sequentially reads the plurality of differential magnetic field signals V_diff with the synchronization of the clock signal CLK, performs parallel-to-serial processing to form a serial enhanced magnetic field signal V_ampli, and uses an output terminal to output the enhanced magnetic field signal to the AD converting module.

In some detailed implementations of exemplary embodiments of the present application, as shown in FIG. 4, the plurality of first magneto-sensitive elements 2211 and the plurality of second magneto-sensitive element 2212 are located on a side of substrate 61 that faces toward the steel cord ply 41, and the plurality of differential circuits 2220 and the signal output module 223 are located on a side of the substrate 61 that faces away from the steel cord ply 41. The signal connection line 70 is not shown in this figure.

In some detailed implementations of exemplary embodiments of the present application, the signal output module 223 and the AD converting module may be connected through the signal connection line 70. In other detailed implementations of exemplary embodiments of the present application, the signal output module 223 and the AD converting module may also include Bluetooth chips to wirelessly transmit the enhanced magnetic field signal V_ampli in the form of Bluetooth through pairing.

By setting the spacing distance (that is, M/2) between the first magneto-sensitive element 2211 and the second magneto-sensitive element 2212 along the moving direction of the steel cord ply 41 as half of the spacing distance M between the adjacent steel cords of the steel cord ply 41 along the moving direction of the steel cord ply 41 to delay the magnetic field signals V1 and V2 output by the first magneto-sensitive element 2211 and second magneto-sensitive element 2212 for half a cycle, and then using the differential circuit 2220 to perform differential processing on V1 and V2, the influence of the background magnetic field and the external interferential magnetic field on the output magnetic field signal can be eliminated, and the magnetic field variation caused by the steel cord ply 41 cutting across the magnetic force line is effectively amplified, thereby greatly improving the signal-to-noise ratio of the output enhanced magnetic field signal.

Figure 7:
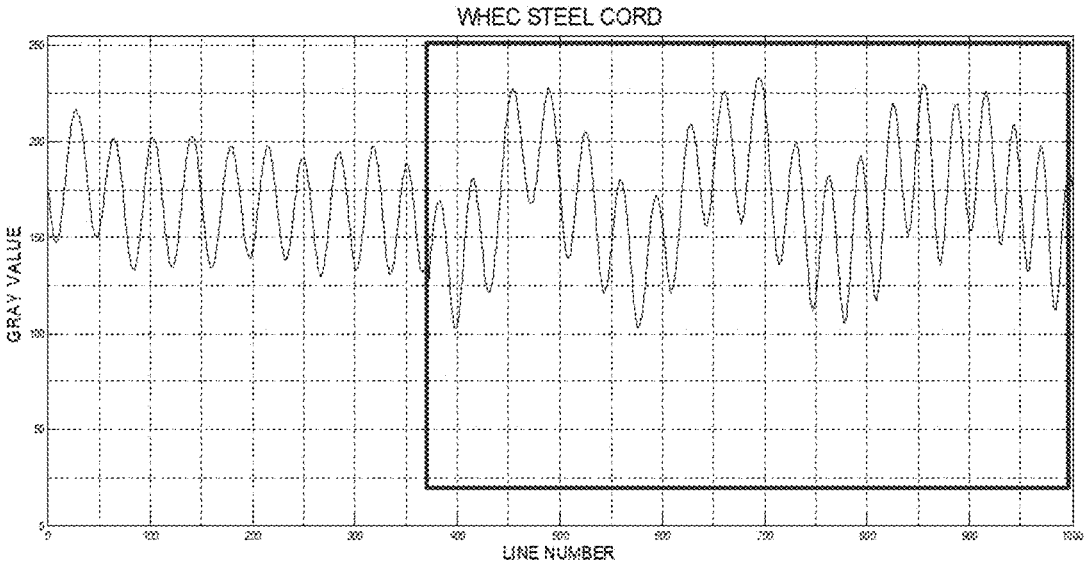
FIG. 7 is a magnetic field signal of a steel cord ply output by a magneto-sensitive element in conventional techniques.
Figure 8:
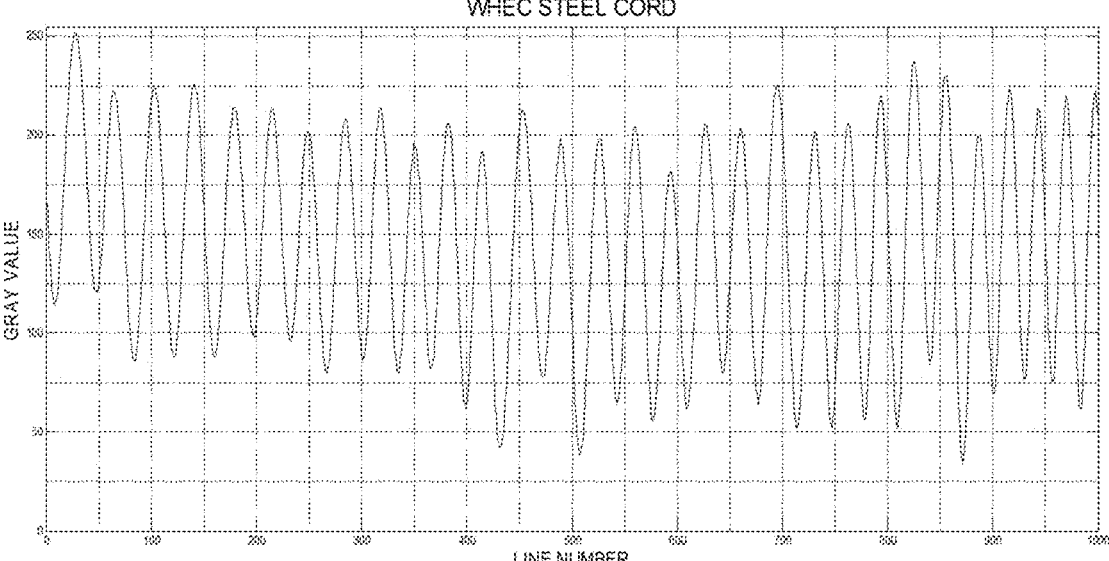
FIG. 8 is a differential magnetic field signal output by a differential circuit according to exemplary embodiments of the present application.

FIG. 7 is a magnetic field signal detected by a single magneto-sensitive element when the steel cord ply 41 is in a motion state, and the line frame part in the figure is a magnetic field signal output where an interferential magnetic field exists; FIG. 8 is a magnetic field signal output after differential processing of a magnetic field signal obtained by paired first magneto-sensitive element 2211 and second magneto-sensitive element 2212 according to exemplary embodiments of the present application. The amplitude of the change of the magnetic field signal in FIG. 8 is about twice the amplitude of the change of the magnetic field signal in FIG. 7. In FIG. 8, the change to the signal amplitude caused by the interferential magnetic field is effectively eliminated, and the magnetic field signal from the background magnetic field part is offset. (it should be noted that the signal shown in FIG. 8 has a reference voltage, which is due to a voltage boost to facilitate subsequent signal processing, rather than the background magnetic field).

At the same time, since the enhanced magnetic field signal is generated by differential amplification of the magnetic field signals at two positions, which means that the enhanced magnetic field signal is only related to the difference of the magnetic field signals at the two positions and has little to do with the specific magnetic field distribution, the problem that the placement of the magnetic field unit 11 in different positions may affect the sensed and output magnetic field signals can be effectively solved. Therefore, the cooperation mode of magnetic field unit 11 and the signal obtaining unit 22 can be flexibly adjusted according to the detection purpose and the actual detection conditions.

Figure 9:
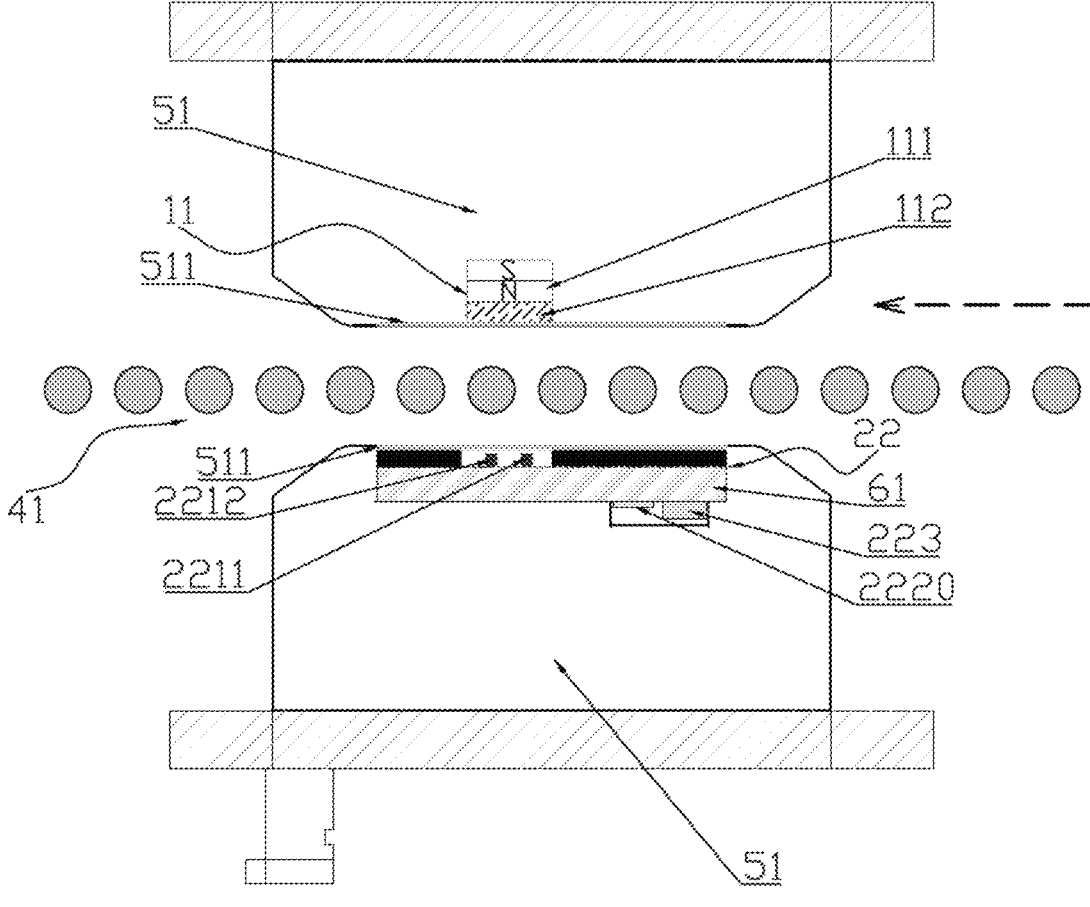
FIG. 9 is an assembled side view of another detailed implementation according to exemplary embodiments of the present application.

FIG. 9 is an assembled side view of another specific implementation of an embodiment of the present application. In this specific implementation, the magnetic field unit 11 and the signal obtaining unit 22 are oppositely arranged on two sides of the steel cord ply 41 and are respectively fixedly installed in the frames 51.

Figure 10:
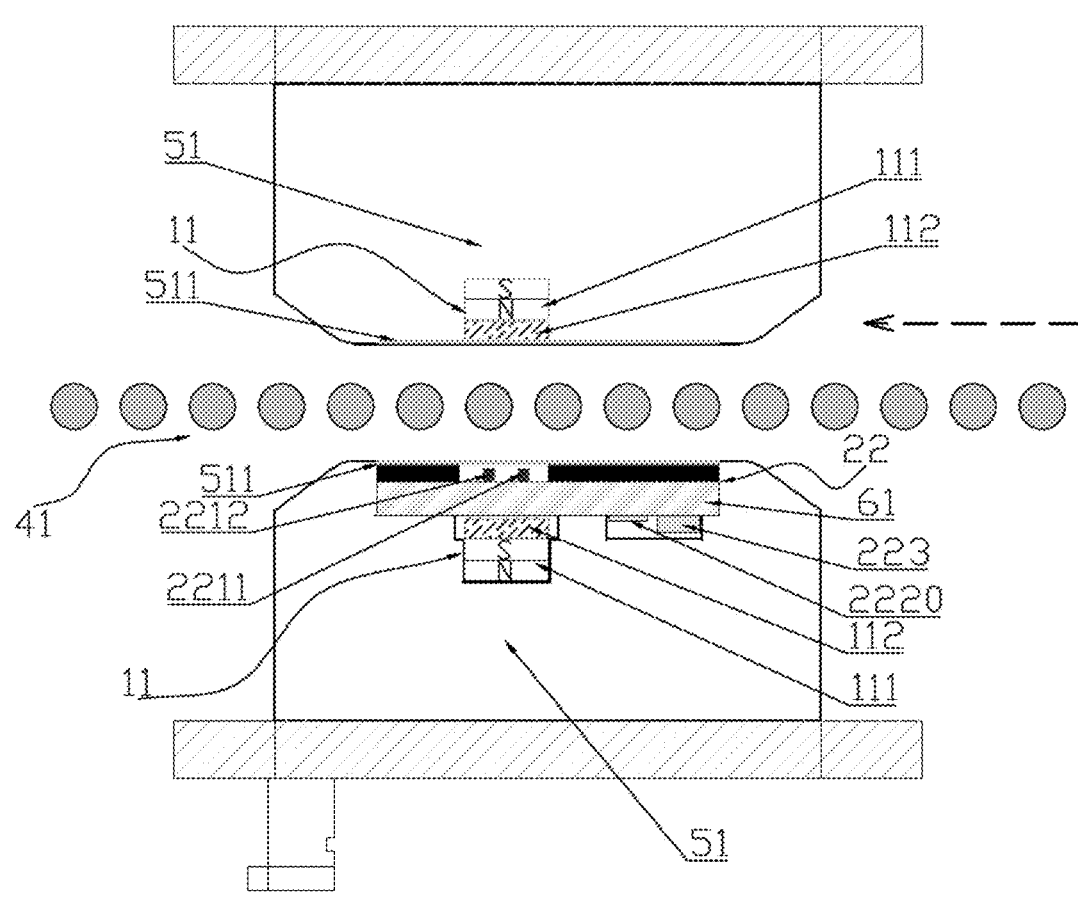
FIG. 10 is an assembled side view of another detailed implementation according to exemplary embodiments of the present application.

FIG. 10 is an assembled side view of another specific implementation of an embodiment of the present application. In this specific implementation, there are two magnetic field units 11, which are oppositely arranged on two sides of the steel cord ply 41, and the signal obtaining unit 22 is located on a line connecting the magnetic field units 11 and is located on the surface of a side of one of the magnetic field units 11 that faces toward the steel cord ply 41. The above-mentioned magnetic field units 11 and the signal obtaining unit 22 are fixedly installed in the frames 51.

In some preferred implementations of embodiments of the present application, as shown in FIG. 4, FIG. 9, and FIG. 10, the surface of a side of the frame 51 facing toward the steel cord ply 41 is a cover 511. The cover is made of a material with high wear resistance to protect the signal obtaining unit 22 and the magnetic field unit 11, and prevent the steel cord ply 41 from abrasion.

The implementation of the defect detecting unit in exemplary embodiments of the present application will be described in detail below with reference to FIG. 2, and FIG. 11 to FIG. 13.

In exemplary embodiments of the present application, as shown in FIG. 2, the defect detecting unit includes an AD converting module, a signal processing module, a defect detecting module, a display module, and a control module.

Figure 11:
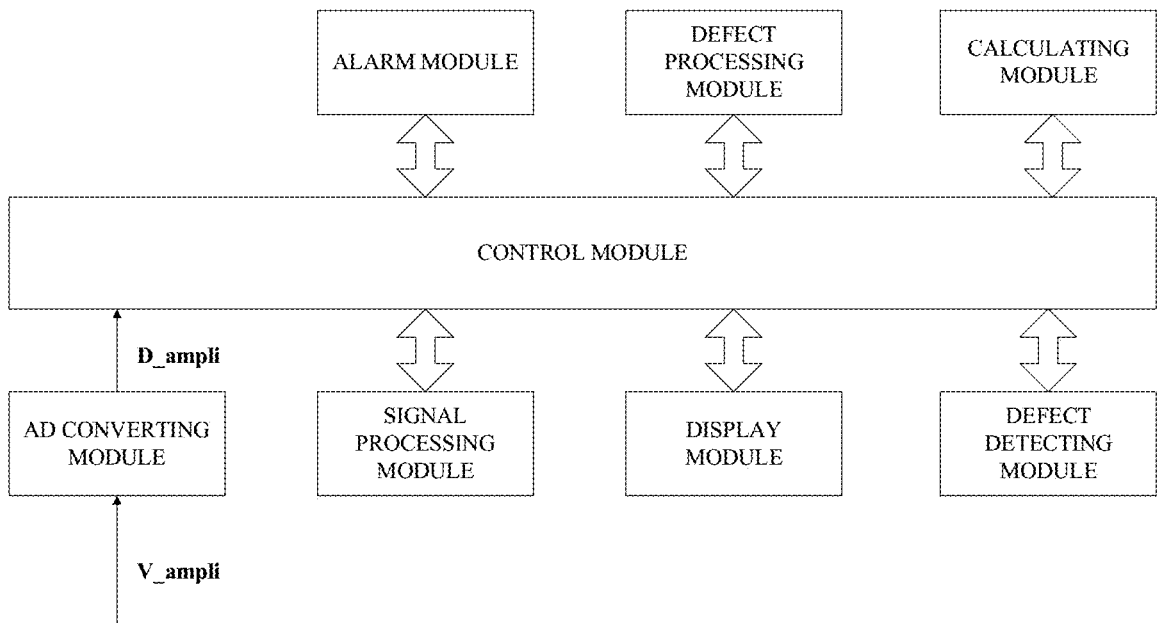
FIG. 11 is a system block diagram of a defect detecting unit according to exemplary embodiments of the present application.

Further, as shown in the system block diagram of the defect detecting unit according to exemplary embodiments of the present application in FIG. 11, the AD converting module is connected to the signal output module 223 (not shown) for converting an enhanced magnetic field signal into a digital magnetic field signal. The signal processing module processes the digital magnetic field signal to generate a magnetic field signal to be detected. The defect detecting module analyzes the magnetic field signal to be detected to generate a defect detection result of the steel cord ply 41. The display module displays the magnetic field signal to be detected and the defect detection result of the steel cord ply 41. The control module is used to control the AD converting module, the signal processing module, the defect detecting module, and the display module.

For example, in exemplary embodiments of the present application, the AD converting module may be connected to the signal output module 223 through the signal connection line 70 or may be connected to the signal output module 223 through a Bluetooth module to receive the serial enhanced magnetic field signal V_ampli. The AD converting module may be an 8-bit AD converter, which converts the serial enhanced magnetic field signal V_ampli into a serial digital magnetic field signal D_ampli with an output range of 0-255 (256 levels in total), or it may be an AD converter with more than 8 bits to divide the output range more precisely.

The signal processing module may include a clock signal interface, which converts a magnetic field digital signal into a magnetic field signal to be detected under the synchronization of the clock signal CLK.

The defect detecting module analyzes the magnetic field signal to be detected and generates a defect detection result of the steel cord ply 41. The defect detection result may include information such as defect position and defect type.

The display module may be a monitor of a desktop computer or a screen of a tablet computer or a notebook computer and may be used to display the magnetic field signal to be detected and the defect detection result.

The control module may be a single-chip microcomputer equipped with a control program or a processor of a desktop computer, a tablet computer, or a notebook computer, and may be used to control the AD converting module, the signal processing module, the defect detecting module, and the display module.

Figure 12:
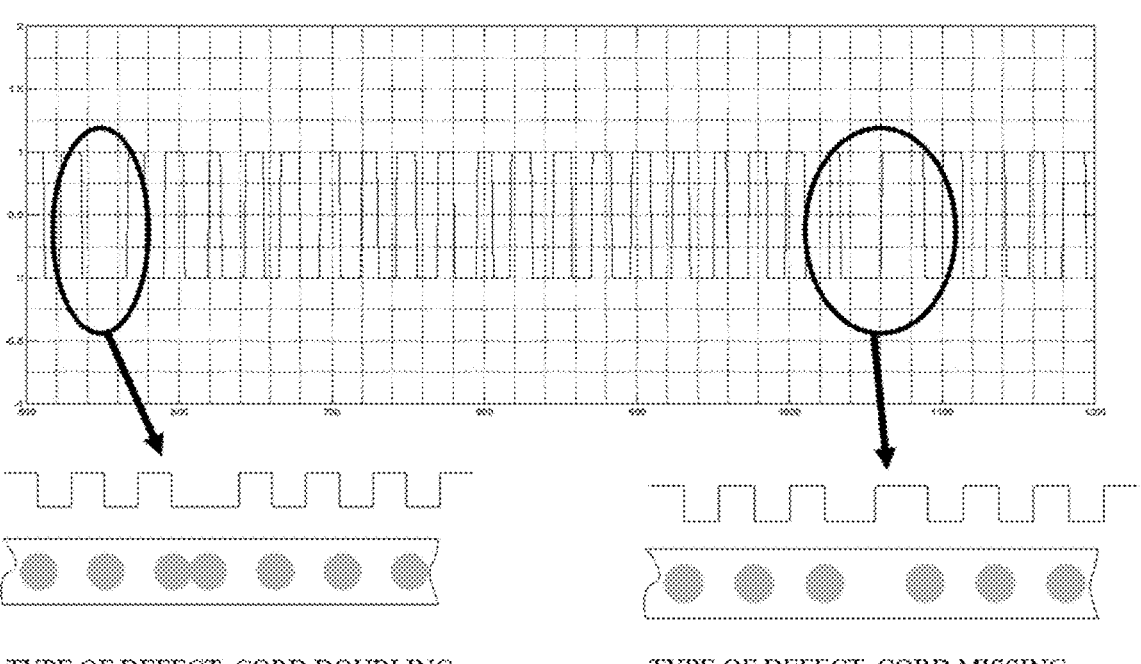
FIG. 12 is a square wave signal of a magnetic field at a certain point of a steel cord ply with defect detection results marked up in a detailed implementation according to exemplary embodiments of the present application.

FIG. 12 shows a magnetic field square wave signal at a certain point of the steel cord ply 41 with defect detection results marked up in a detailed implementation of an embodiment of the present application. In this detailed implementation, the signal processing module performs threshold judgment and binarization on a digital magnetic field signal D_ampli to generate a square waveform of magnetic field signals to be detected at multiple positions. The defect detecting module analyzes the square wave to generate a defect detection result. The defect detection result may include the position of the defect and the type of the defect. The display unit displays the magnetic field signals to be detected at multiple positions in the form of square waves, and the defect detection result.

Figure 13:
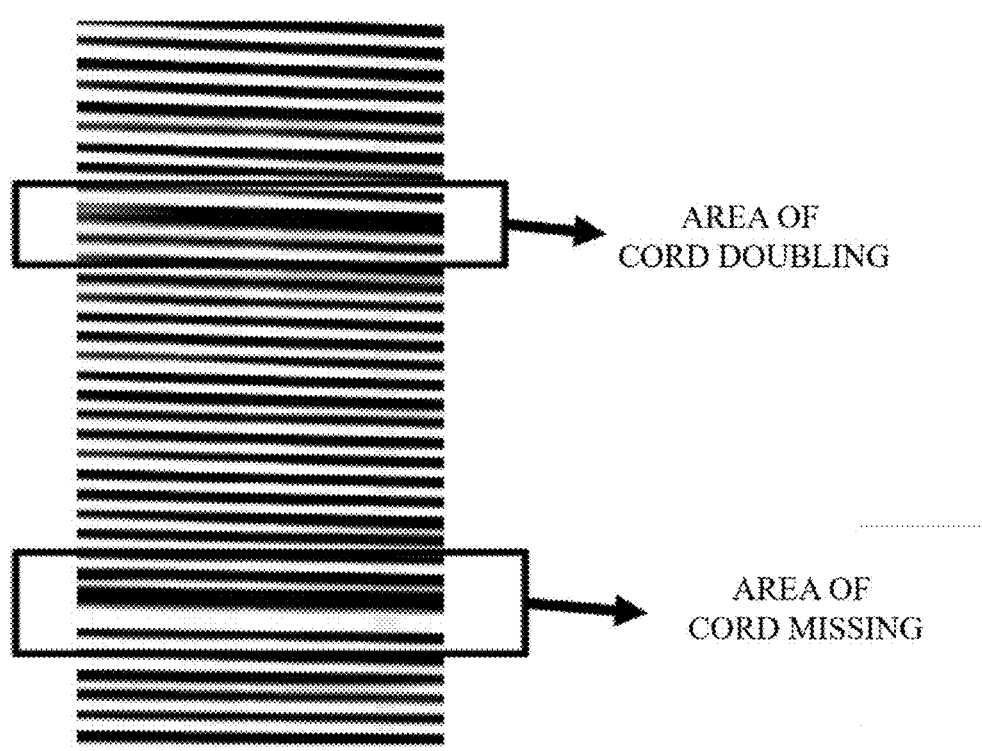
FIG. 13 is a magnetic image of a steel cord ply with defect detection results marked up in another detailed implementation according to exemplary embodiments of the present application.

FIG. 13 shows a magnetic image of the steel cord ply 41 with defect detection results marked up in another detailed implementation of an embodiment of the present application. In this detailed implementation, the signal processing module converts a serial digital magnetic field model D_ampli to a magnetic image of the steel cord ply 41 in the form of a grayscale image, which is used as the magnetic field signal to be detected. The defect detecting module analyzes the magnetic image and generates a defect detection result. The defect detection result may include the position and type of the defect. The display unit displays the magnetic image of the steel cord ply 41, which is used as the magnetic field signal to be detected, and the defect detection result.

Further, as shown in FIG. 11, the defect detecting unit further includes: a calculating module, which determines defect marking information according to a detection result of the defect of the steel cord ply 41 and the moving speed of the steel cord ply 41, where the defect marking information includes mark position information and mark trigger time; a defect processing module, which puts a mark on a defect according to the defect mark information; and an alarm module for abnormal alarm.

The detailed implementation of the present application has been described in detail above. For those skilled in the art, without departing from the principle of the present application, some improvements and modifications can be made to the present application, and these improvements and modifications also fall within the scope of protection of the claims of the present application.

What is claimed is:

1. A device for detecting a defect of a steel cord ply, configured to obtain an enhanced magnetic field signal of the steel cord ply and detect a defect of the steel cord ply based on the enhanced magnetic field signal, comprising:

a magnetic field unit including a permanent magnet configured to generate a background magnetic field;

a signal obtaining unit configured to generate an enhanced magnetic field signal of a steel cord ply based on a plurality of first magnetic field signals and a plurality of second magnetic field signals, wherein the signal obtaining unit includes:

a magnetic sensor module configured to generate the plurality of first magnetic field signals and the plurality of second magnetic field signals, a differential module connected to the magnetic sensor module and configured to generate a plurality of differential magnetic field signals based on the plurality of first magnetic field signals and the plurality of second magnetic field signals, and a signal output module connected to the differential module and including input terminals configured to receive the plurality of differential magnetic field signals and at least one output terminal, wherein the signal output module is configured to generate and output the enhanced magnetic field signal based on the plurality of differential magnetic field signals; and a defect detecting unit configured to detect a defect in the steel cord ply based on the enhanced magnetic field signal, wherein the defect detecting unit includes an AD converting module, a signal processing module, a defect detecting module, a display module, and a control module;

wherein a width of a cross-section of the permanent magnet along a moving direction of the steel cord ply is smaller than a spacing distance between adjacent steel cords of the steel cord ply along a moving direction of the steel cord ply;

wherein the magnetic sensor module includes:

a plurality of first magneto-sensitive elements configured to sense a change of a magnetic field caused by a movement of the steel cord ply in the background magnetic field and generate the plurality of first magnetic field signals; and a plurality of second magneto-sensitive elements configured to sense a change of a magnetic field caused by the movement of the steel cord ply in the background magnetic field and generate the plurality of second magnetic field signals, wherein the plurality of first magnetic field signals and the plurality of second magnetic field signals are electrical signals;

wherein the plurality of first magneto-sensitive elements correspond to the plurality of second magneto-sensitive elements in a one-to-one way, and a spacing distance between each first magneto-sensitive element and a corresponding second magneto-sensitive element along a moving direction of the steel cord ply is half of a spacing distance between adjacent steel cords of the steel cord ply along the moving direction of the steel cord ply.

2. The device according to claim 1, wherein the plurality of first magneto-sensitive elements is distributed at intervals along a direction perpendicular to the moving direction of the steel cord ply; and the plurality of second magneto-sensitive elements are distributed at intervals along a direction perpendicular to the moving direction of the steel cord ply.

3. The device according to claim 2, wherein the differential module includes a plurality of differential circuits, and the plurality of differential circuits are connected to the plurality of first magneto-sensitive elements and the plurality of second magneto-sensitive elements in one-to-one correspondence; and one end of the differential circuit is connected to the first magneto-sensitive element, and the other end of the differential circuit is connected to the second magneto-sensitive element, and output terminals of the plurality of differential circuits are connected to the input terminals of the signal output module.

4. The device according to claim 1, wherein the magnetic field unit further includes a magneto-conductive plate located on a surface of a side of the permanent magnet that faces toward the steel cord ply, and the magneto-conductive plate is made of a magneto-conductive material.

5. The device according to claim 1, wherein the AD converting module is connected to the signal output module and configured to convert the enhanced magnetic field signal into a digital magnetic field signal;

the signal processing module is configured to process the digital magnetic field signal to generate a magnetic field signal to be detected;

the defect detecting module is configured to analyze the magnetic field signal to be detected and generates a defect detection result of the steel cord ply;

the display module is configured to display the magnetic field signal to be detected and the defect detection result of the steel cord ply; and the control module is configured to control the AD converting module, the signal processing module, the defect detecting module, and the display module.

6. The device according to claim 5, wherein the defect detecting unit further includes:

a calculating module configured to determine defect marking information according to the defect detection result of the steel cord ply and a moving speed of the steel cord ply, wherein the defect marking information includes mark position information and a mark trigger time;

a defect processing module configured to mark a defect according to the defect marking information; and alarm module configured to implement anomaly alerting.

7. The device according to claim 1, further comprising a frame, wherein the magnetic field unit and the signal obtaining unit are fixedly installed in the frame.

8. The device according to claim 7, wherein a surface of a side of the frame that faces toward the steel cord ply is a cover.

\* \* \* \* \*